United States Patent [19]

Livingston et al.

[11] Patent Number: 4,561,444
[45] Date of Patent: Dec. 31, 1985

[54] IMPLANTABLE CARDIAC PACER HAVING DUAL FREQUENCY PROGRAMMING AND BIPOLAR/LINIPOLAR LEAD PROGRAMMABILITY

[75] Inventors: John H. Livingston, Coral Gables; Barry M. Yomtov, Pembroke Pines, both of Fla.

[73] Assignee: Cordis Corporation, Miami, Fla.

[21] Appl. No.: 618,767

[22] Filed: Jun. 11, 1984

Related U.S. Application Data

[63] Continuation of Ser. No. 291,430, Aug. 10, 1981, abandoned.

[51] Int. Cl.⁴ .............................................. A61N 1/36
[52] U.S. Cl. ................................................ 128/419 PG
[58] Field of Search ....... 128/419 P, 419 PG, 419 PS, 128/419 PT

[56] References Cited

U.S. PATENT DOCUMENTS

| | | | |
|---|---|---|---|
| 3,311,111 | 3/1967 | Bowers | 128/422 |
| 3,478,746 | 11/1969 | Greatbatch | 128/419 PG |
| 3,557,796 | 1/1971 | Keller, Jr. et al. | 128/419 |
| 3,718,909 | 2/1973 | Greatbatch | 128/419 PT |
| 3,727,616 | 4/1973 | Lenzkes | 128/422 |
| 3,805,796 | 4/1974 | Terry, Jr. et al. | 128/419 P |
| 3,833,005 | 9/1974 | Wingrove | 128/419 P |
| 3,870,050 | 3/1975 | Greatbach | 128/419 PG |
| 3,920,024 | 11/1975 | Bowers | 128/419 PG |
| 4,019,518 | 4/1977 | Maurer et al. | 128/419 R |
| 4,192,316 | 3/1980 | Walters et al. | 128/419 PG |
| 4,202,342 | 5/1980 | Keller, Jr. | 128/419 PG |
| 4,203,447 | 5/1980 | Keller, Jr. et al. | 128/419 PG |
| 4,300,566 | 11/1981 | Stindt et al. | 128/419 PG |

FOREIGN PATENT DOCUMENTS

| | | | |
|---|---|---|---|
| 985797 | 3/1965 | United Kingdom | 128/419 PG |
| 2026870 | 2/1980 | United Kingdom | 128/419 PG |

Primary Examiner—William E. Kamm
Attorney, Agent, or Firm—Henry W. Collins; George H. Gerstman

[57] ABSTRACT

The stimulation output of an implanted cardiac pacer is applied between a cathode at the end of a pacer lead in the heart and an anode whose location is programmable. An electronic switch accessed via programming designates the pulse generator case as the anode for an additional electrode located near the end of the pacer lead, thus changing the pacer from unipolar to bipolar operation or vice-a-versa after implantation. Different programming pulse rates are used to program different functional characteristics. For example, pulses at one rate select mode, high or low frequency range, sensitivity and anode location while pulses at another frequency set the pulse generation rate and output current.

4 Claims, 9 Drawing Figures

IMPLANTABLE CARDIAC PACER HAVING DUAL FREQUENCY PROGRAMMING AND BIPOLAR/UNIPOLAR LEAD PROGRAMMABILITY

CROSS-REFERENCE TO RELATED APPLICATIONS

This application is a continuation of U.S. patent application Ser. No. 291,430, filed Aug. 10, 1981, now abandoned.

This application is related to the following U.S. patent applications, assigned to the assignee of the present application, each of which is incorporated in its entirety herein:

"Multi-Mode Microprocessor-Based Programmable Cardiac Pacer", Leckrone et al., U.S. patent application Ser. No. 207,003, filed Nov. 14, 1980, now U.S. Pat. No. 4,485,818; and "Interactive Programmer for Biomedical Implantable Devices", Mumford et al., U.S. patent application Ser. No. 281,011, filed July 6, 1981, now U.S. Pat. No. 4,432,360.

BACKGROUND OF THE INVENTION

The invention relates generally to programmable implantable biomedical devices.

Programming in the context of this application means noninvasively transferring parameter value data from an external device called the programmer to an internal device implanted in the patient's body. A number of systems have been successfully employed in commercially available cardiac pacers, including magnetic programming and radio frequency (RF) programming. One of the problems addressed by the present invention is expanding the number and range of parameters programmable by pulse counting techniques such as have been used in the past in Cordis Omnicor ® cardiac pacers.

Cardiac pacers are life supporting, therapeutic medical devices. They are surgically implanted and remain in a living person's body for years. The vital considerations in cardiac pacing technology tend to dictate a conservative approach. Thus, while pulse counting techniques are less efficient at transmitting data than more sophisticated pulse coding techniques, they have proven extremely reliable over many years of service.

The typical implanted cardiac pacer operates by supplying missing stimulation pulses on a pacing lead attached to the ventricle. The so called R-wave can be sensed by the same lead. An additional lead contacts the atrium to sense P-waves, if desired. In programmable pacers, the fixed rate at which the pulse generator will produce pulses may be selected from among a variety of optional rates, for example, from forty to one hundred beats per minute. It is desirable to have as many rates available as is practical for two reasons. First, it enhances the physician's ability to match the pacer to the patient so as to avoid angina and to coordinate the fixed rate with the patient's normal sinus rythm. Secondly, the higher the rate, the shorter the life time of the pacer battery. By the same token, it is desirable to have a number of different pulse intensities available for selection. Pulse intensity is programmed either by adjusting pulse width or pulse current. It is generally desirable to minimize the pulse intensity to minimize tissue damage which changes the contact resistance and to conserve power.

The stimulation output of the pulse generator is applied to the heart via two electrodes, namely, a cathode and anode. Typically the cathode for ventricular pacing is located at the top of an elongated insulated pacing lead which extends pervenously into the right ventricle of the heart. The electrical return path to the anode can be achieved in two different ways. The case of the pulse generator can be used as the anode. In this system since only one electrode is located at the end of the pacer lead, the lead is called "unipolar". In the other system, the anode as well as the cathode are located at the end of the pacer lead which is referred to as a "bipolar" lead in this case.

In the past, cardiac pacers and pacing leads have been available in either unipolar or bipolar configuration. The anode location was irreversibly selected at implantation. If a unipolar lead was implanted, and it was determined that capture could be more easily obtained with a bipolar lead or if there were muscular twitching in the vicinity of the pulse generator, the patient had to undergo a new operation to replace both the lead and the pulse generator.

SUMMARY OF THE INVENTION

The general purpose of the invention is to expand the range and number of parameters which can be programmed in a biomedical implantable device. Different programming pulse rates are used to program different functional characteristics. For example, pulses at one rate select mode, high or low frequency range, sensitivity and anode location while pulses at another frequency set the pulse generation rate and output current.

In the preferred embodiment, a programming transmission consists of a group of pulses at a 3 millisecond pulse repetition rate followed by a second faster group of pulses with a period of 1.5 milliseconds. The two groups of pulses are discriminated by corresponding bandpass filters which direct the respective pulse group to conventional pulse counting and decoding circuitry. In the preferred embodiment, a previously used standard pulse repetition frequency is used in the first group of programming pulses to program previously available pulse parameters including selection of a stimulation frequency within each range and selection of the output current. The second pulse group is used to select the high or low frequency range, the sensitivity of the sense amplifier for sensing natural cardiac activity one of three modes, VVO, VVI or VVT in the conventional notation, and finally to designate the anode location as either the pulse generator case or a second electrode on the pacing lead.

DESCRIPTION OF THE PREFERRED EMBODIMENT

Figure 1:
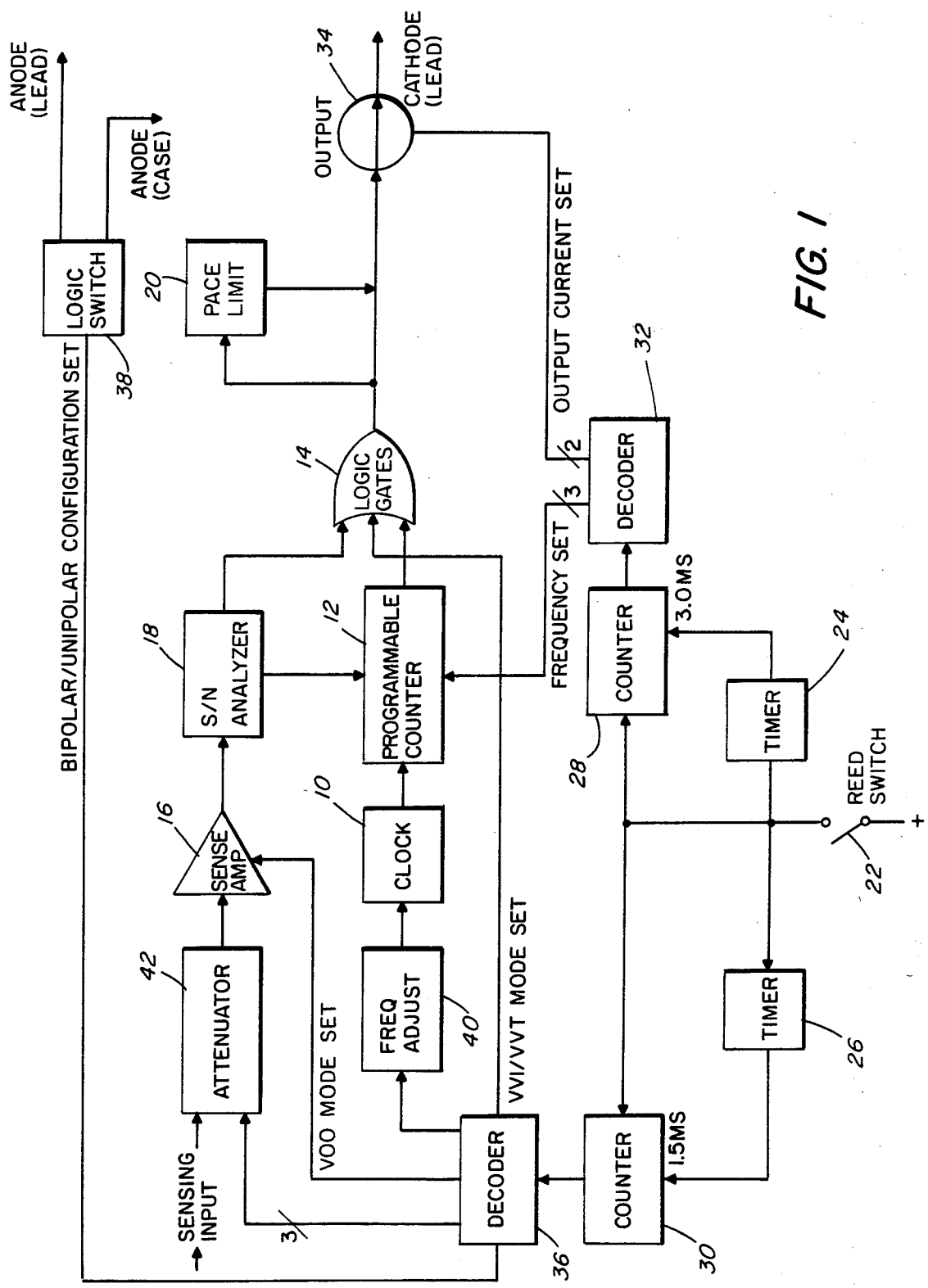
FIG. 1 is a block diagram illustrating the electronic circuitry housed in the implanted pulse generator of the cardiac pacer according to the invention.

FIG. 1 illustrates in functional form the overall electronic circuit requirements for bipolar/unipolar pacing and programming in the pulse generator portion of an implantable cardiac pacer according to the invention. The electrical components of the pacer are intended to be powered by a two-cell lithium compound battery and sealed together with the battery cells in the customary biologically compatible hermetic enclosure such as a welded titanium case with an integral connector formed of tissue compatible epoxy. The pacer or pulse generator as it is often called is implanted subcutaneously preferably in the pectoral, axilliary or abdominal regions. The pulse generator is electrically interconnected with a pacer lead which extends through an opening in a nearby vein into the heart, terminating against the lower interior wall of the right ventricle.

The circuitry of FIG. 1 is designed to provide long term cardiac pacing while offering the physician the option of being able to alter the load, lead configuration and sensitivity as well as the output current and fixed rate of the implanted pacer. A cardiac pacer including the circuitry of FIG. 1 according to the invention is being introduced to the market by Cordis Corporation, the assignee of the present application, under the trademark Multicor Gamma, Model No. 336A. The pacer parameters are designed to be altered by employing an external portable battery powered Model 222C Omnicor Programmer which emits electromagnet pulses in a code recognized by the pacer programming circuitry. Programming can be accomplished with the programmer at any time before, during or after implantation.

In the preferred embodiment, the circuitry of FIG. 1 is designed to achieve the following programmable parameters.

Output Current: 1, 2, 4 or 7 milliamps (mA)
Fixed Rates: 25, 30, 35, 40, 45, 50, 55, 60 70, 80, 90, 100, 110, 120 pulses per minute (ppm)
Sensitivity: 0.8, 1.5, 2.5, 3.0, 3.5, 4.0, 5.0 or 5.5 millivolts (mV)
Pacer Modes: VVI (R-wave inhibited), VVT (R-wave synchronous) or VOO (asynchronous or fixed rate)
Lead Configuration: Bipolar or unipolar In the circuit of FIG. 1, the pacer clock 10 produces logic pulses at a steady rate. Clock pulses are counted by the programmable counter 12, which also divides the count by one of eight ratios before providing outputs to the logic gates 14 at fixed fractions of the pacers pulse to pulse interval. The logic gates develop the refractory, noise sampling, and alert portions of the pacer timing cycle and also initiate the pacer output pulse at the appropriate time. These timing functions are similar to those found in commercially available Omnicor ® pacers. When enabled in either the VVI or VVT mode, the programmable sensing amplifier 16 detects cardiac depolarizations and produces a logic pulse approximately 10 milliseconds wide each time the input signal exceeds the amplifier threshold in either the positive or negative direction. In the VVI and VVT modes, the signal/noise analyzer 18 is activated for noise detection during the final portion of the refractory period. If electrical noise is received by the pacer during the refractory period, the analyzer provides a control signal that causes the pacer to complete the balance of the timing cycle and then produce an output pulse. If noise is not detected during the final portion of the refractory period, the analyzer 18 accepts single logic outputs from the sensing amplifier 16 at the beginning of the alert period. If such an output is received, the analyzer 18 resets the counter 12 and immediately begins a new timing cycle.

The pace limit circuit 20 measures the interval between pacer output pulses and limits the minimum spacing to approximately 400 ms. Thus, if the output pulse rate tends to increase because of a circuit malfunction, for example, the maximum rate will be limited to approximately 150 ppm. At approximately 150 Ppm, the pace limit circuit is designed to block 2:1, to produce an actual rate of approximately 75 ppm. If the internal rate continues to increase, the pace limit circuit will again operate to allow the actual output rate to increase up to approximately 150 ppm and then will block 3:1. Higher internal rates will be blocked proportionately 4:1, 5:1 etc., to always limit the output pulse rate to approximately 150 ppm. The abrupt decrease in rate following an increase in rate provides an indication to the patient that the pace limit circuit has been activated. The pace limit function is independent of the other pacer circuits and has no effect on normal pacer operation. However, in the VVT mode, the pace limit circuit prevents stimulation at rates above 150 ppm caused, for example, by the patient's intrinsic heart rate or by an external pacer.

The remaining components of FIG. 1 accomplish the setting of the various parameter values set forth above. Magnetic pulse trains from an external programmer actuate the reed switch 22 during each programming transmission sequence, causing voltage pulses to be conducted to the timing circuits 24 and 26 and pulse counters 28 and 30. Two successive programming transmissions are required to set all programmable parameters. The programmer used in connection with the pacer circuitry of FIG. 1 differs from prior Cordis Omnicor ® programmers only in the provision of selectable means for generating pulses at twice the normal rate of 3 ms. By design, in the first transmission, pulses occur at a pulse repetition period of approximately 3.0 ms; in the second transmission, the pulse repetition period is 1.5 ms.

Rate and output current are programmed during the first lower frequency transmission. The 3 ms pulses are counted in binary pulse counter 28. As a safety feature, as in U.S. Pat. No. 3,805,796 to Terry et al., assigned to the assignee of the present application, the counters 28 and 30 cannot be activated until eight pulses have been received at the respective pulse repetition rate. Once enabled, counter 28 may count up to 32 successive pulses 3 ms apart. The sum of the pulses counted at the first frequency determines which of the five binary output lines of decoder 32 will be activated. Three of the output lines are used to set the programmable counter for rate programming, and two of the lines are used to establish the output current level by setting the operating characteristics of the output driver circuit 34. During the second transmission at 1.5 ms pulse repetition period, the voltage pulses from the reed switch 22 are passed by the timing circuit 26 and counted in the other binary counter 30, once enabled by the reception of eight initial pulses. Counter 30 is designed to count up to 128 successive pulses. The sum determines which of the seven binary output lines of decoder 36 will be activated. One output line of decoder 36 determines circuit configuration by setting logic switch 38 to designate the anode. Another line determines the high or low range of the frequency adjust circuit 40. Clock 10 is an RC controlled oscillator whose inherent period of oscillation is determined by a discharge of current. Frequency adjust circuit 40 causes more or less current to be drained from the discharge circuit so as to set the output frequency of the clock 10 at a higher level or a lower level. As a consequence, all of the intervals established by the programmable counter 12 and logic gates 14 are automatically adjusted to a high or a low range. The resulting fixed rate output of the pacer is one of the two-clock frequencies (high rate range or low rate range) as determined by frequency adjust circuit 40, divided by one of eight programmable counter ratios selected via decoder 32 in the first transmission. Three binary output lines of the decoder 36 determine the sensitivity of the pacer to natural cardiac activity. Sensitivity is programmed by setting the attenuator 42 to one of eight levels by manipulating a bank of resistors with electronic switches or transmission gates responsive to the binary output lines. The remaining two lines from the decoder 36 determine the pacing mode. If the VOO mode set line is high, the sense amplifier 16 is disabled thus making the pacer independent of natural cardiac activity. The other binary output line of decoder 36 selects VVI or VVT mode. In the normal VVI mode, an R-wave occurring during the alert period as sensed by the sense amplifier 16 restarts the timing cycle without stimulation. This is the normal demand mode or Stanicor ®mode of operation. In the R-wave synchronous (VVT) mode, the sensing of an R-wave during the alert period causes the pacer to superimpose instantaneously a stimulation pulse as well as restarting the timing cycle. As in the Ectocor ® mode, a brief interval at the start of the alert period is arranged to inhibit stimulation while resetting the timing interval.

The timing circuits 24 and 26 at the inputs to the program counters 28 and 30 are safety devices. They are activated when the first magnetic pulse of each pulse train is received. If another pulse does not occur within approximately 3 ms (or 1.5 ms), the timing circuits will turn off the counters and hold the program decoder output lines in the previously programmed state. Thus, stray magnetic pulses from the environment cannot by themselves change the program. As in the Terry patent, an enable counter precedes the program counter/decoder circuit. Thus, it is the enable counter which is reset and not the program counter/decoder, when another pulse does not occur within the required pulse period.

Figure 2:
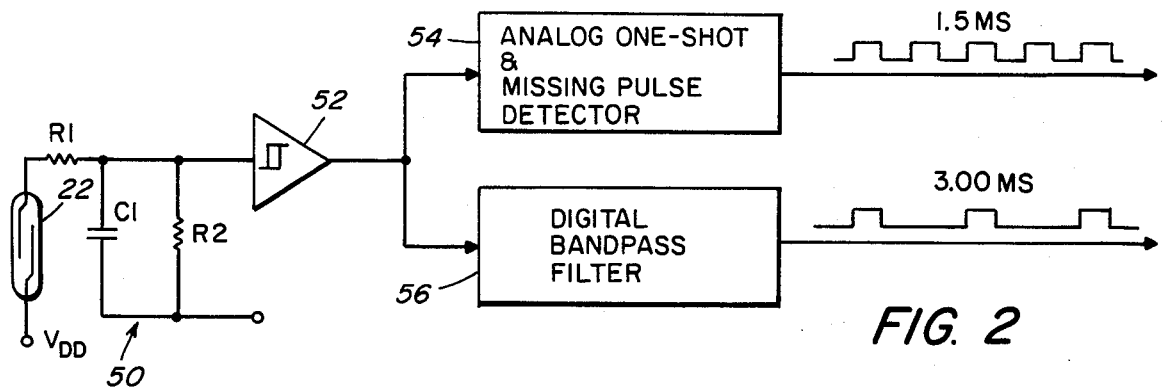
FIG. 2 is an electrical schematic and block diagram illustrating the programming data input circuitry of FIG. 1 in more detail.
Figure 3:
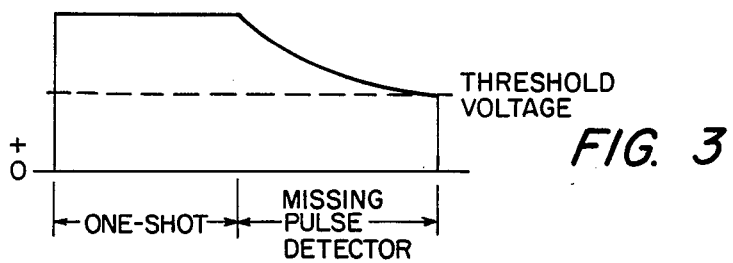
FIG. 3 is a graph of voltage versus time illustrating the output of the analog one-shot and missing pulse detector of FIG. 2.
Figure 4:
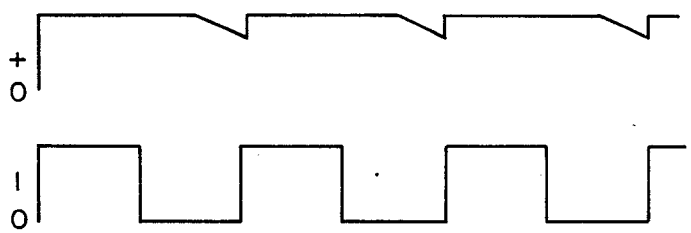
FIGS. 4, 5 and 6 are similar composite timing diagrams illustrating the output of the analog one-shot and missing pulse detector of FIG. 2 for normal pulse rate, excessively slow pulse rate and excessively fast pulse rate, respectively.
Figure 5:
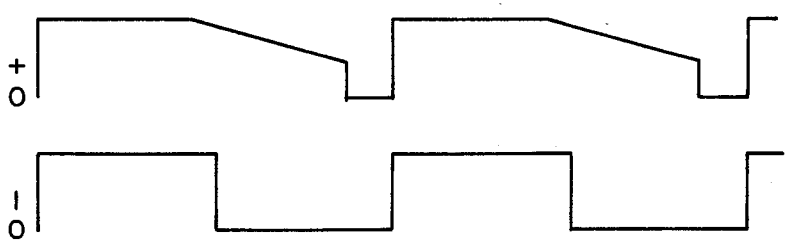
Figure 6:
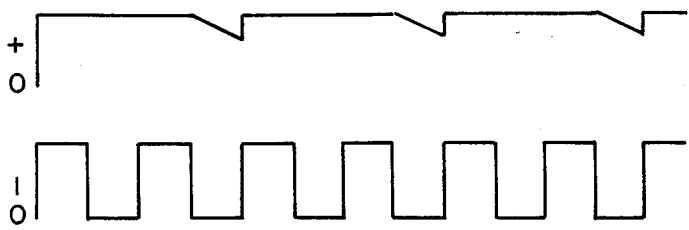

Multi-frequency programming requires frequency discrimination in the programming circuits. This is accomplished by the timing circuitry 24 and 26 which is shown in more detail in FIG. 2. One side of the reed switch 22 is connected to positive voltage $V_{DD}$. The other side is connected by an isolation resistor R1 and an RC debounce filter 50 to the input of a Schmitt trigger 52 which accomplishes the necessary pulse shaping. Debounce filter 50 comprises capacitor C1 and resistor R2 connected in parallel from the junction of resistor R1 and Schmitt trigger 52 to ground $V_{SS}$. The performance characteristics of the filter are determined by the value of capacitor C1 which in the preferred embodiment is 470 picofarads. The discharge time constant must be fast in order for the input signal to return below the threshold before the next pulse. The time constant is determined by setting the resistor value R2, preferably approximately 500 kilohms. Resistor R1 is preferably about 1 kilohm to isolate $V_{SS}$ from $V_{DD}$. The dual frequency programming system necessitates the respective counters 28 and 30 be programmed independently at 3 and 1.5 ms respectively. For this reason, it is necessary that the tolerances of the bandpass circuitry be chosen with care. The output of the Schmitt trigger 52 is a series of pulses at either 3.0 ms or 1.5 ms. As shown in FIG. 2, timing circuitry 26 is implemented by means of an analog one-shot and missing pulse detector 54. The bandpass characteristics of this analog filter are determined by the RC time constants in these two conventional circuits (not shown). The leading edge of the program input signal triggers the one-shot as shown in FIGS. 3 thru 6. When the one-shot circuit times out, the missing pulse detector begins to discharge the voltage level. When the voltage level has discharged to a threshold voltage, the enable counter (not shown) is reset so that programming cannot occur. This corresponds to the condition where the pulse repetition rate is too low as in FIG. 5. If the leading edge of the next pulse occurs when the one shot is still high, the pulse is not counted as shown in FIG. 6. If the leading edge of the next pulse occurs before the decaying voltage reaches the threshold level, the oneshot is retriggered and the counter is advanced as shown in normal operation in FIG. 4. The band width for the 1.5 ms pulses. It has been determined that the optimum band width for the 1.5 ms pulses using this system of detector 54 is 465 to 1250 hertz (Hz).

Figure 7:
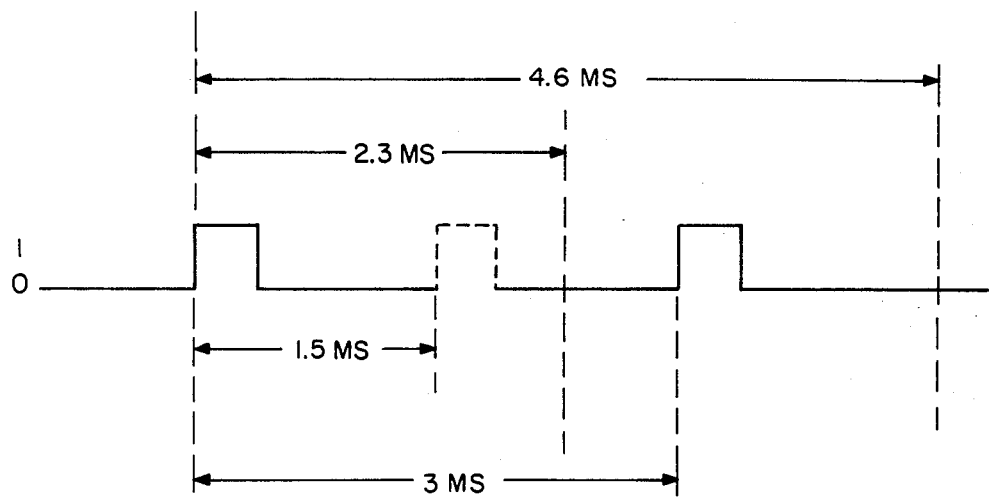
FIG. 7 is a timing diagram illustrating the time window implemented by the digital bandpass filter of FIG. 2 for the slower programming rate.

The lower frequency pulses discriminated by timing circuitry 24 are passed through a corresponding digital bandpass filter 56. In the preferred embodiment, the digital bandpass filter, as shown in FIG. 7, is designed to cause the enable counter to be reset unless the pulse interval is between 2.3 ms and 4.6 ms corresponding to a lower bandpass of 215 to 434 Hz. The digital bandpass filter may be implemented by employing a special counter which counts clock pulses from a special program clock preferably having a rate of approximately 1613 Hz. The counter is enabled by the leading edge of the first magnetic programming pulse. The leading edge of the next programming pulse samples the count and resets the counter. If the sampled count is 4, 5, 6 or 7 clock pulses, the pulse interval is acceptable. If the sampled count is anything other than 4 through 7, the enable counter is reset thus retaining the previous count in the program counter.

Figure 8:
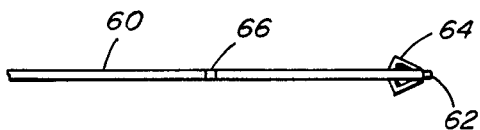
FIG. 8 is a schematic representation of a plan view of the end of a bipolar pacing lead of the type with which the circuit of FIG. 1 is designed to be used.

Because of the programmable lead configuration feature, the pacer circuitry of FIG. 1 is designed to be used in connection with a bipolar pacing lead. As shown in FIG. 8, a suitable bipolar pacing lead comprises a pair of conductors extending through a polyurethane insulating sheath 60 terminating in a cathode tip 62 made of platinum-irridium. Just behind the cathode tip 62 collapsible silastic fins 64 help anchor the pacer lead in the trebeculae of the heart chamber. Approximately 3.7 centimeters away from the tip a ring electrode 66 also of platinum-irridium is available to serve as a remote anode. The electrodes 62 and 66 on the pacer lead are electrically connected to the ends of the respective conductors in the sheath 60.

Figure 9:
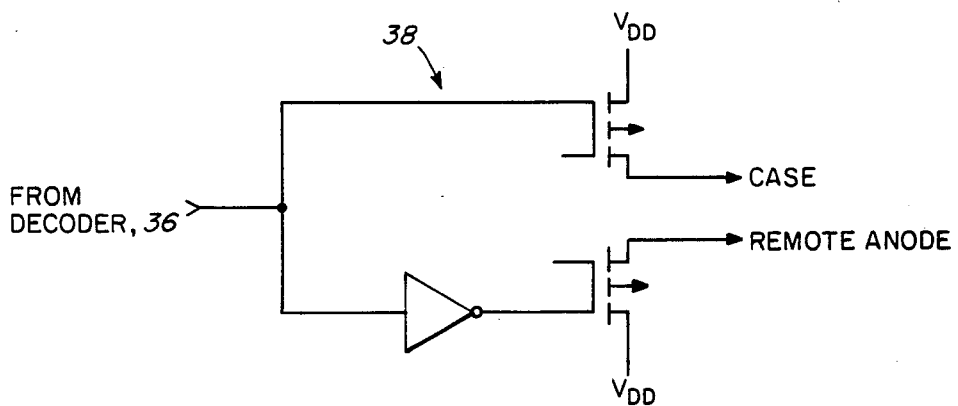
FIG. 9 is an electrical schematic diagram of the bipolar/unipolar logic switch.

As shown in FIG. 9, the unipolar/bipolar logic switch 38 can be implemented by switching the connection of positive voltage $V_{DD}$ to the case of the implanted pulse generator or the remote anode 66 of FIG. 8. The single bit output line from decoder 36 to the logic switch 38 is divided into a pair of complementary outputs to control the gates of two p-channel V-MOS or D-MOS fuel defect transistors of the type available from Supertex, Inc. This type of transistor is chosen as an electronic switch because of its extraordinarily low drain to source "ON" resistance since it will be in series with the heart's impedance.

The advantage of this unique system is that it allows changing of the electrode arrangement after implantation of the pulse generator. Such a change previously required either a replacement electrode or alteration of the pulse generator electronics connector. In either case, surgery was required.

The multi-frequency programming system described above is not limited to dual frequency programming. It may be extended to any number of frequencies so long as suitable bandpass filter arrangements can be made. The multi-frequency programming system offers the capability of increasing the transmitted data to the pulse generator without increasing the number of programming pulses at one frequency. The system is thus particularly suitable for adding programmable functions to a given pacer. By adjusting the passband, the new programmable functions can be implemented affecting the operation of the original programming system.

The foregoing description is intended to be illustrative rather than restrictive, the scope of the invention being indicated by the appended claims.

What is claimed is:

1. An implantable cardiac pacer having a multi-frequency programming system, comprising
    first and second registers,
    first means responsive exclusively to an externally generated programming signal at a lower frequency for decoding said lower frequency signal and storing a corresponding number in said first register,
    second means responsive exclusively to an externally generated signal at a higher frequency for decoding said higher frequency signal and storing a corresponding number in said second register,
    pulse generator means for producing output stimulation pulses at a variable rate, and
    means respinsive to the numbers stored in both said first and second registers for iniquely determining the rate of said pulse generator.

2. The pacer of claim 1, wherein said pulse generator means includes
    adjustable clock means for producing clock pulses at a selected clock rate,
    means for selecting said clock rate in accordance with the number stored in said first register,
    programmable counter means for repeatedly counting a predetermined number of said clock pulses to divide the clock pulse rate by a corresponding factor, and
    means for selecting the predetermined number for said programmable counter means in accordance with the number stored in said second register.

3. The system of claim 1, wherein each of said first and second means responsive exclusively to externally generated signals includes a respective bandpass filtering means, counting means connected to receive and count the output of said bandpass filtering means for retaining a count representing the most recently transmitted programming data from said bandpass filtering means and decoding means for producing a plurality of parallel binary outputs corresponding to the number stored in said counting means.

4. The system of claim 3, wherein the center frequency of the pass band of the second filtering means is at least approximately double that of the first filtering means.

* * * * *

UNITED STATES PATENT AND TRADEMARK OFFICE
CERTIFICATE OF CORRECTION

PATENT NO. : 4,561,444
DATED : December 31, 1985
INVENTOR(S) : John H. Livingston and Barry M. Yomtov It is certified that error appears in the above-identified patent and that said Letters Patent are hereby corrected as shown below:

In the Title: Change "linipolar" to -- unipolar --.

Column 4, line 20, change "Ppm" to -- ppm --.

Column 8, line 10, change "respinsive" to -- responsive --.

Column 8, line 11, change "iniquely" to -- uniquely --.

Signed and Sealed this

Eighth Day of July 1986

[SEAL]

Attest:

DONALD J. QUIGG

Attesting Officer

Commissioner of Patents and Trademarks